Figure 1:
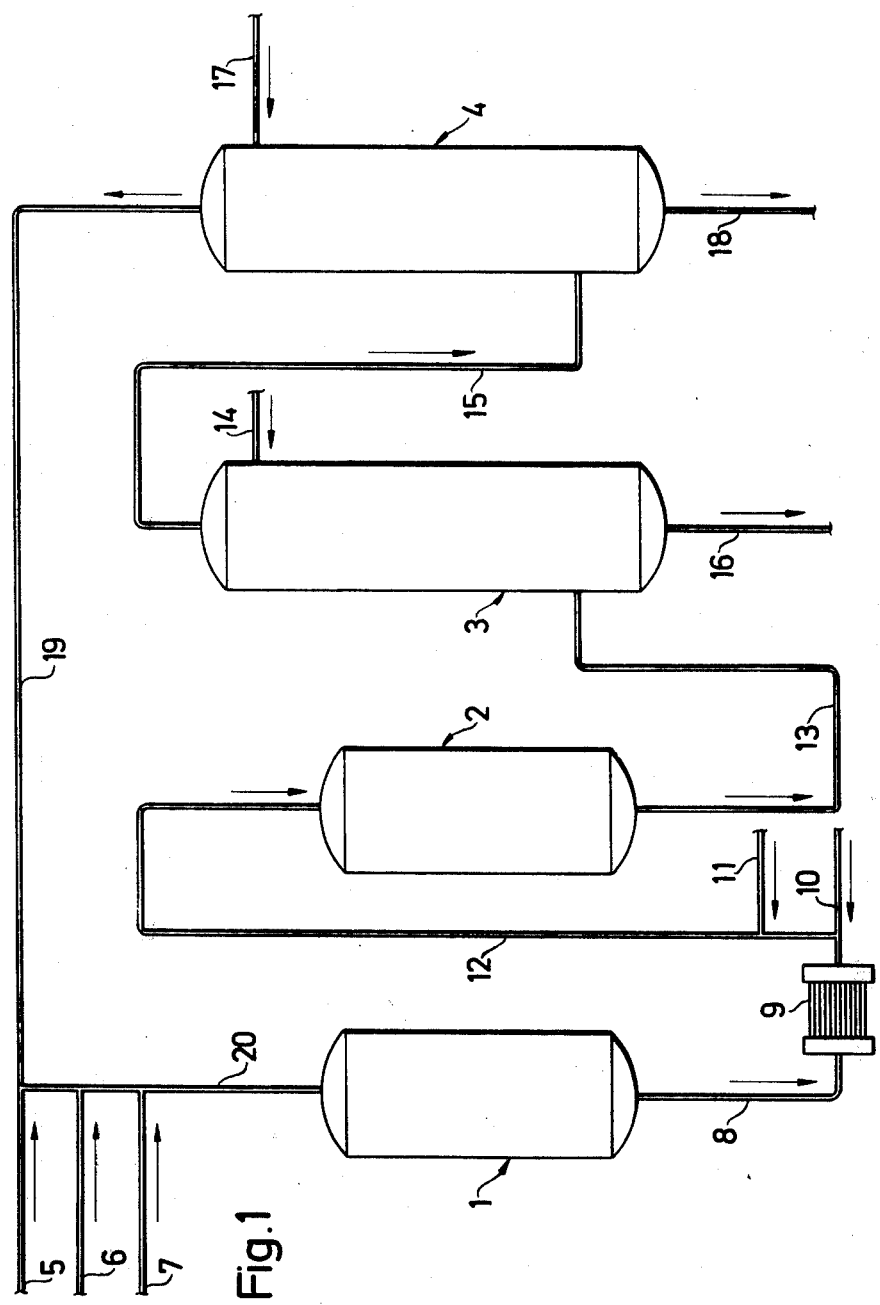

United States Patent [19]

Cocuzza et al.

[11] 4,055,579
[45] Oct. 25, 1977

[54] PROCESS FOR THE PRODUCTION OF ETHYLENE OXIDE

[75] Inventors: Gioacchino Cocuzza, Catania; Italo Montoro, Como; Benedetto Calcagno, Milan, all of Italy

[73] Assignee: Societa' Italina Resine S.I.R. S.p.A., Milan, Italy

[21] Appl. No.: 420,343

[22] Filed: Nov. 29, 1973

[30] Foreign Application Priority Data

Nov. 30, 1972 Italy .................................. 32274/72

[51] Int. Cl.$^2$ .......................................... C07D 301/10
[52] U.S. Cl. ............................................... 260/348.34
[58] Field of Search ..................................... 260/348.5

[56] References Cited

FOREIGN PATENT DOCUMENTS

| 1,055,147 | 1/1967 | United Kingdom |
| 1,134,318 | 11/1968 | United Kingdom |

*Primary Examiner*—Norma S. Milestone
*Attorney, Agent, or Firm*—Sughrue, Rothwell, Mion, Zinn and Macpeak

[57] ABSTRACT

Ethylene oxide is prepared by supplying a gaseous mixture containing ethylene, oxygen and a moderator of the oxidation reaction to a first reaction zone containing a silver-based catalyst, cooling the gas stream leaving this zone, supplying it after enrichment with oxygen and moderator to a second reaction zone containing the silver-based catalyst, recovering ethylene oxide and recycling the residual gases after being combined with fresh reacting gases, the reaction temperature of the second zone being at least 5° C less than the temperature of the first zone.

16 Claims, 2 Drawing Figures

PROCESS FOR THE PRODUCTION OF ETHYLENE OXIDE

BACKGROUND OF THE INVENTION

1. FIELD OF THE INVENTION

The present invention relates to an improved process for the production of ethylene oxide and relates more particularly to the preparation of ethylene oxide by reacting ethylene with oxygen on silver-based catalysts.

2. DESCRIPTION OF THE PRIOR ART

As is known, in the direct oxidation of ethylene to ethylene oxide a gaseous mixture containing relatively small quantities of ethylene and oxygen is conveyed over a silver-based oxidation catalyst.

Catalytic oxidation is usually brought about at temperatures of approximately 150° to 400° C and at pressures varying from atmospheric pressure to approximately 30 atmospheres. The catalyst contains silver which is usually deposited on a granular support such as mullite, silica, alumina, silicon carbide, magnesium oxide or the like. The catalyst can also contain smaller quantities of other metals such as platinum, gold, palladium, barium and calcium. The latter substances are called activators of the ethylene oxidation reaction.

As is known, in the aforementioned process of oxidation only a part of the ethylene is converted to ethylene oxide and more or less charge quantities of total oxidation products, such as water and carbon dioxide, are formed.

Consequently, the gaseous reaction products are treated in order to separate by-products other than ethylene oxide, after which the residual gas stream is recycled to the oxidation reactor.

There are various prior-art methods of obtaining reaction gases rich in ethylene oxide and reducing as much as possible the amounts of by-products in the ethylene oxidation reaction. A high content of ethylene oxide in the reaction gases is desirable, both for reasons of productivity and because it is easier to recover the gases. A low quantity of by-products indicates both a low consumption of valuable products and a simplification of that part of the apparatus which is used for eliminating the by-products.

Various methods of obtaining these desirable results have been tried in the prior art, e.g., the use of improved catalysts or the supply of special substances together with the reacting gases, the special substances either modulating the oxidation reaction or varying the method of oxidizing ethylene.

Attempts, for example, have been made to influence the catalyst, either by carefully choosing the support, or by varying the manner in which silver is precipitated on the support. As is known, the properties of the carrier and of the deposited silver have an important effect on the activity and selectivity of the catalyst in the oxidation reaction of ethylene to ethylene oxide.

It is also known in the prior art to use special substances having a moderating effect on the ethylene oxidation reaction. In general organic compounds containing halogen or nitrogen are used as moderators.

These compounds are used in very small quantities and prevent the organic compounds in the reaction mixture from being completely oxidized.

In other known methods, the oxidation of ethylene to ethylene oxide is made more productive by partially replacing the inert gas in the gaseous supply mixture by paraffins (usually methane) containing a small number of carbon atoms. Methane, which restricts the explosive zone, enables the gaseous supply mixture to contain higher concentrations of reagents.

Finally, the conditions under which ethylene is oxidized, more particularly the temperature control, are also important. As is known, relatively large quantities of heat are generated during the ethylene oxidation reaction and tend to increase the temperature both of the gas and of the catalyst. Consequently, unless the heat of the reaction is rapidly removed, hot points develop on the catalyst, with a consequent further increase in the heat developed owing to the increased speed of the reaction. The final effort is a reduction of the yield of ethylene oxide through complete combustion to carbon dioxide and water.

The usual method of avoiding hot points is to limit the maximum temperature of the oxidation reaction so as to control the speed at which heat is developed in the reactor. The temperature can also be controlled by using reactors consisting of a number of tubes filled with catalyst and surrounded by a cooling medium.

The aforementioned precautions can improve the method of oxidizing ethylene to ethylene oxide but have not produced completely satisfactory results. The known methods cannot increase productivity, i.e., the concentration of ethylene oxide in the reaction gases, beyond a relatively modest limit without undesirably increasing the by-products, i.e., without causing an reduction of the selectivity of the reaction.

This is due at least partly to the fact that it has not been possible to effectively influence the course of the temperature in the reaction zone, more particularly in those methods using a single oxidation reactor, and to the fact that it has not been possible to make complete use of the properties of the aforementioned moderators in the ethylene oxidation reaction.

SUMMARY

One object of the present invention is to provide an improved process for the production of ethylene oxide by oxidizing ethylene in the presence of silver-based catalysts, which yields reaction gases having high concentrations of ethylene oxide and small quantities of by-products. Further objects will be apparent from the following description:

The process according to the invention essentially consists in oxidizing ethylene to ethylene oxide on a silver-based catalyst in two separate reaction zones connected in series, and in maintaining in each zone the temperature and the concentrations of the reagents and of the moderator in the gas stream supplied to the zones under control.

More particularly, in the method according to the invention, a gaseous mixture containing ethylene, oxygen and a moderator of the oxidation reaction is supplied to a first reaction zone containing the silver-based catalyst. On leaving this zone, the gas stream is first cooled and then enriched with oxygen or a gas containing molecular oxygen and moderator and is supplied to a second zone containing the silver-based catalyst. On leaving the second zone, the gases are treated to recover the ethylene oxide and separate it from by-products, and are then recycled to the first zone after being combined with fresh reacting gases.

According to an important feature of the process according to the invention, the conversion in the first oxidation zone is limited so that the content of ethylene oxide in the outgoing gas stream does not exceed about 1.5% by volume.

According to another important feature of the invention, different oxidation temperatures are maintained in the two reaction zones, so that the temperature in the second zone is at least 5° C less than the temperature of the first zone.

The term "reaction temperature" denotes the average temperature of the bath cooling the reactor.

According to another important feature of the process according to the invention, the gas stream leaving the first reaction zone is enriched with oxygen or oxygen-containing gas and with a moderator of the oxidation reaction. Finally, according to another essential feature, the contact times are kept relatively long, and are always equal to, or greater than, one second in each of the two reaction zones.

It has been found that the aforementioned method, under conditions which will be described hereinafter, can yield reaction gases leaving the second reaction zone containing up to 2.2% by volume of ethylene oxide, the total selectivity of the reaction being greater than 70%.

The term selectivity is defined as follows:

$$\frac{\text{Mols of ethylene converted to ethylene oxide}}{\text{Total mols of converted ethylene}} \times 100$$

In the accompanying FIG. 1, references 1 and 2 denote ethylene oxidation reactors. The reactors comprise tube nests containing the catalyst in the tubes and a cooling medium outside the tubes.

The catalysts used for the present purposes are those obtained in industry by decomposing a decomposable silver salt on a granular support and contain about 7 to 30% by weight of silver with respect to the support.

The catalysts are preferably obtained by decomposing silver lactate on alpha-alumina which has been activated by treatment at a temperature above 1000° C and which has a surface area of about 0.01 to 1.0 m²/g, a porosity of about 10 – 40% and an average pore diameter of about 30 to 150 microns. The support is generally used in the form of spherules of about 4 to 9 mm in diameter.

In the accompanying FIG. 1, reactor 1 is supplied through pipe 20 with a gaseous mixture containing ethylene, oxygen and a moderator for the oxidation reaction. More particularly, according to the invention, the ethylene content of the gaseous mixture is maintained at values in the range of from about 5 to 25% by volume and the oxygen content is kept at values of from about 2 to 10% by volume.

The preferred values for ethylene and oxygen are about 8 to 20% and from 5 to 8% by volume, respectively.

The gas stream supplied to the first reactor also contains a moderator for the oxidation reaction. The moderator, which is present in quantities of about 0.1 to 20 ppm, is selected from those commonly used in the art which have previously been defined. The preferred moderators are: organic halogenated, more particularly chlorinated, compounds, more particularly dichloroethane.

In addition to ethylene, oxygen and the moderator, the gas stream contains an inert substance such as nitrogen and may also contain varying quantities of methane.

Ethane, on the other hand, is undesirable in the present process, and the content thereof in the reaction gases should be kept very low. In practice, the stream supplying the first reactor consists of a recycled gas stream (pipe 19 in FIG. 1) to which fresh oxygen and ethylene besides the moderator are added (pipes 5, 6, 7 respectively in FIG. 1). The ethylene used for this purpose has a purity of about 99.5% and is obtained e.g., from plants for pyrolysing naphtha with water vapour. Oxygen having a purity higher than 99% or, preferably, the commercial product having a purity of from 90 to 99% can be used.

The first reactor operates at temperatures of about 220° to 350° C and at pressures varying from atmospheric pressure to about 30 kg/cm². Preferably the temperatures and pressures are from about 270° to 290° C and from about 15 to 20 kg/cm². Reaction times of about 1 to 6 seconds are maintained in reactor 1.

Under the conditions described, a flow of gas wherein the concentration of ethylene oxide is equal to, or less than, 1.5% by volume and is usually between 0.9 and 1.3% by volume, is discharged from reactor 1 through pipe 8. The gas is first cooled to temperatures of from about 220° to 270° C in a heat-exchanger 9 and then enriched with oxygen and with the moderator for the oxidation reaction.

More particularly, with reference to FIG. 1, pipe 10 supplies a stream of oxygen gas or oxygen-containing gas. To this end, oxygen having a purity greater than 99% or, preferably, a commercial product having a purity of from 90 to 99% can be used.

According to another embodiment, oxygen-containing gas, e.g. a mixture of oxygen and nitrogen, is supplied.

Pipe 11 supplies one of the moderators previously described.

In each case the supply rates are adjusted so that reactor 2 is supplied through pipe 12 with a gas stream containing about 2 to 10% by volume, preferably about 5 to 8% by volume, of oxygen and about 0.1 to 20 ppm, preferably about 1 to 5 ppm, of moderator.

According to an essential feature of the process according to the invention, the temperature of reactor 2 is kept at least 5° C lower than that of reactor 1. More particularly, the operating temperature in reactor 2 is from about 200° to 300° C, preferably from about 260° to 280° C, and the pressures are approximately equal to those described in connection with reactor 1.

In the second reaction step, the contact time is from about 1 to 6 seconds.

Under the aforementioned conditions, a gas stream containing up to 2.2%, usually from 1.5 to 2.0%, by volume of ethylene oxide and showing an increase in carbon dioxide of less than 2% with respect to the stream supplied through pipe 20, is discharged from reactor 2 through pipe 13.

Referring again to FIG. 1, the gas stream taken from line 13 is first cooled and then supplied to the bottom of column 3.

An aqueous solvent is supplied to that column 3 through pipe 14. Consequently, an aqueous solution enriched in ethylene oxide is withdrawn through pipe 16 and is treated to recover the ethylene oxide. The gas stream withdrawn from column 3 through pipe 15 is supplied to column 4, where it is treated to eliminate the carbon dioxide produced in the reaction.

To this end, a solution adapted to block carbon dioxide is supplied through pipe 17. The residual gases are withdrawn at the top of column 4 through pipe 19 and recycled to reactor 1 after being combined with fresh reagents and the moderator for the oxidation reaction.

Before recycling the gas stream a purification — although to a minor extent — is provided for in order to prevent increases in the concentration of substances such as nitrogen and argon which cannot be eliminated by other means.

It will be remembered that the particularly advantageous results obtainable by the process according to the invention are due at least partly to the particular method of using the moderator and to the ability to control the temperature of the two reaction steps independently. The moderators (or substances inhibiting the undesired total combustion of the organic compounds), more particularly the chlorinated organic compounds, are subject to complex degradation and deterioration along the catalyst bed. For example, dichloroethane is partially converted to vinyl chloride and corresponding polymers, which are deposited on the catalyst and on the inner surface of the reactor tubes. The decomposition products have a low capacity to inhibit the total oxidation reaction. Consequently, the end portion of the catalyst bed is inadequately influenced by the moderator.

It is essential, therefore, to restore the moderator in an intermediate zone of the catalyst bed, i.e., in the process according to the invention, at an intermediate point between the two oxidation reactors.

According to the invention, the temperature is independently controlled in the two reaction zones.

More particularly, the two reactors can be temperature-controlled either by a flow of cooling fluid or by a fluid evaporating along the jacket.

Figure 2:
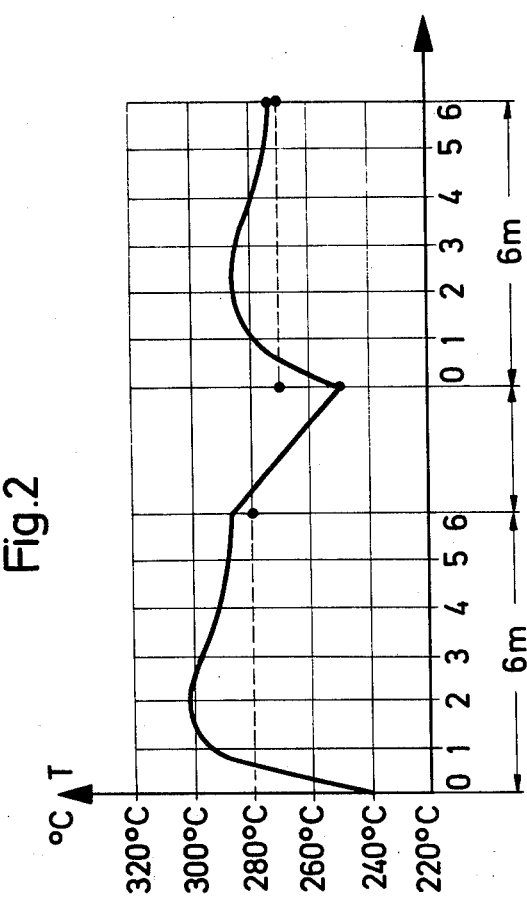

As FIG. 2 shows, the reacting gas stream is initially preheated to the temperature at which the speed of the ethylene oxidation reaction reaches values at which remarkable quantities of heat are generated. A rapid increase in temperature then occurs, resulting from the high initial concentrations of reagents, which cause a high reaction speed. Within certain limits, the speed of the reaction is proportional to the concentration of reagents (ethylene and oxygen).

When the reagents, more particularly the oxygen, get exhausted, the speed of the reaction, and simultaneously the amount of heat liberated, decrease, with a consequent decrease in the heat gradient between the gas and the thermostatizing liquid.

At the outlet of the first reactor, therefore, the oxygen concentration is restored to its initial level by adding to the mixture a stream of oxygen or of an oxygen-containing gas mixture. As already mentioned, fresh moderator is also added at this place. After being enriched in this way, the mixture is supplied to the second reaction step.

Before entering the second reaction zone, cooling is provided for in the intermediate reaction step with the purpose of cooling the gas and preventing that the temperature of the first layers of catalyst in the second reaction zone is increased so as to produce thermal peaks resulting in the total combustion of the ethylene and ethylene oxide contained in the gases. Next, the second reaction zone is kept at a lower temperature than the first zone, so that the ethylene is epoxidized under gentler conditions, in order to prevent substantial quantities of ethylene oxide from undergoing further oxidation.

The invention is further illustrated by the following non-limiting examples:

EXAMPLE 1

With reference to FIG. 1, the recycled gas stream from pipe 19 is enriched with oxygen (90% pure) through pipe 5 and with ethylene (99.8% pure) through pipe 6.

The moderator (a flow of nitrogen saturated with dichloroethane) is supplied through pipe 7.

Consequently, the gas stream supplied to reactor 1 through pipe 20 contains 6% by volume of oxygen, 15% by volume of ethylene and 3 ppm of dichloroethane, the remainder substantially comprising nitrogen and smaller quantities of other gases such as argon and carbon dioxide.

On entering reactor 1, the gas stream is at a temperature of 240° C and a pressure of 20 kg/cm².

Reactor 1 comprises a nest of tubes 6 meters high, containing catalyst inside the tubes.

The tubes were surrounded by a diathermic fluid which kept them at an average temperature of 280° C.

The catalyst in the first (and also the second) reactor comprises silver deposited on alpha-alumina which had been activated by heating to 1100° C and had a surface area of less than 1 m²/g.

The catalyst was also obtained by impregnating pellets of alpha-alumina with a solution of silver lactate in lactic acid, drying the impregnated substance und subjecting it to heat treatment at temperatures increasing to 280° C.

The finished catalyst also contained 12.8% by weight of silver.

The space velocity in reactor 1 is kept at 10,000 hours$^{-1}$ and the temperature pattern in the reactor is stabilized as shown in FIG. 2.

More particularly, the maximum temperature is about 300° C, which is not high and which results from the considerable linear velocity of the gas stream, resulting in high heat exchange coefficients.

The concentration of ethylene oxide in the gas stream leaving reactor 1 through pipe 8 is 1.2% by volume, the selectivity of the reaction being 70%. The concentration of ethylene in the outflowing gas is 13.3% by volume.

The gas stream is cooled from 285° to 250° C in the heat recovery unit 9, in which a corresponding amount of vapour was produced.

A stream of oxygen (90% pure) is also supplied through pipe 10 so as to restore the concentration of oxygen in the gas mixture to 6% by volume.

Similarly, dichloroethane is supplied through pipe 11 until the quantity in the gas mixture is 4 ppm.

The resulting gas mixture is supplied to reactor 2 through pipe 12.

More particularly, the second reactor, which is identical with reactor 1, is kept at a lower temperature than the first reactor, the temperature of the heat-exchanging fluid being kept at 270° C.

The temperature pattern of reactor 2 is stabilized as shown in FIG. 2.

In the aforementioned method, the gas stream leaving reactor 2 through pipe 13 contains 2% by volume of ethylene oxide, the total selectivity of the oxidation reaction being 72%.

Finally, the reaction products are separated from the by-products in the gas stream. More particularly, ethylene oxide was recovered in tower 3 by absorbing it in aqueous solution, which was supplied through pipe 14.

Finally the gas stream is purified from carbon dioxide by caustic washing in tower 4.

The remaining gas stream is recycled through pipe 19. A purification to a minor extent is also provided for, to prevent the accumulation of substances such as argon and nitrogen, which cannot be eliminated by other means.

EXAMPLE 2

The method is the same as in Example 1, oxygen having 99.5% purity by volume being supplied through pipe 5 and ethylene having 99% purity by volume being supplied through pipe 6.

More particularly, the stream of ethylene contained 0.6% by volume of ethane and 0.3% by volume of methane.

In order to maintain an ethane content of about 1.5% in the reaction gases, 40% purification is carried out with respect to the volume of ethylene supplied.

Since part of the nitrogen was eliminated by the same process, fresh nitrogen was supplied through pipe 10 in a gas mixture containing 60% by volume of oxygen (99.5% pure) and 40% nitrogen (99% pure).

All the other conditions are the same as in the first Example. The second reactor yields reaction gas containing 2.05% by volume of ethylene oxide, the total selectivity of the reaction being 70%.

What is claimed is:

1. Process for the production of ethylene oxide by catalytic oxidation of a gas stream containing ethylene and oxygen in the presence of a silver-based catalyst, characterized in that:

a first reaction zone containing the silver-based catalyst is supplied with a gas stream containing about 5 to 25% by volume of ethylene, about 2 to 10% by volume of oxygen and about 0.1 to 20 ppm of a moderator for the reaction, the zone being kept at a temperature of about 220° to 350° C and at a pressure from atmospheric pressure to about 30 kg/cm$^2$ and the contact times being from about 1 to 6 seconds wherein the conversion in the first zone is limited so that the content of ethylene oxide in the outgoing gas stream does not exceed about 1.5% by volume;

the gas stream from the first zone, containing at least about 0.9% by volume of ethylene oxide, is cooled to about 220° to 270° C and (is added with) oxygen or a gas containing molecular oxygen and the moderator for the reaction are added thereto in such amounts that the concentrations of the aforementioned substances are restored to approximately their respective levels present before entering the first zone and therefore are respectively from about 2 to 10% by volume and from about 0.1 to 20 ppm;

the resulting gas stream is supplied to a second reaction zone containing the silver-based catalyst and the contact times in the second zone are from about 1 to 6 seconds, the pressure is from atmospheric pressure to about 30 kg/cm$^2$ and the temperature is from about 200° to 300° C, the reaction temperature of the second zone being at least 5° C less than the temperature of the first zone; and ethylene oxide leaving the second reaction zone is recovered and the residual gases are recycled to the first zone after removing the carbon dioxide which they contain.

2. A process according to 1, characterized in that the gas stream being supplied to the first reaction zone contains about 8 to 20% by volume of ethylene.

3. A process according to 1, characterized in that the gas stream being supplied to the first reaction zone contains about 5 to 8% by volume of oxygen.

4. A process according to 1, characterized in that the operating temperatures in the first reaction zone are from about 270° to 290° C.

5. A process according to 1, characterized in that the operating pressures in the first reaction zone are from about 15 to 20 kg/cm$^2$.

6. A process according to 1, characterized in that the gas stream leaving the first reaction zone is enriched with oxygen up to values of about 5 to 8% by volume.

7. A process according to 1, characterized in that the gas stream leaving the first reaction zone is enriched with the moderator for the reaction up to values of about 1 to 5 ppm.

8. A process according to 1, characterized in that the operating temperature in the second reaction zone is from about 260° to 280° C.

9. A process according to 1, characterized in that the operating pressure in the second reaction zone is from about 15 to 20 kg/cm$^2$.

10. A process according to 1, characterized in that the ethylene supplied has a purity of about 99.5%.

11. A process according to 1, characterized in that the oxygen supplied has a purity greater than 99% or is commercial oxygen having a purity of about 90 to 99%.

12. A process according to claim 1, characterized in that the silver-based catalyst contains about 7 to 30% by weight of silver with respect to the support.

13. A process according to claim 12, characterized in that the silver-based catalyst is obtained by decomposing silver lactate on alpha-alumina which has been activated by treatment at a temperature above 1000° C and which has a surface area of about 0.01 to 1.0 m$^2$/g, a porosity of about 10–40% and an average pore diameter of about 30 to 150 microns, the support being in the form of spherules of about 4 to 9 mm in diameter.

14. A process according to claim 1, characterized in that the moderator is an organic halogenated compound.

15. A process according to claim 14, characterized in that the organic halogenated compound is dichloroethane.

16. A process according to claim 1, characterized in that the conversion in the first oxidation step is limited so that the content of ethylene oxide in the outgoing gas stream is between 0.9 and 1.3% by volume.

* * * * *